United States Patent
Jensen

(10) Patent No.: US 8,078,780 B2
(45) Date of Patent: Dec. 13, 2011

(54) COMMUNICATIONS METHOD, IN PARTICULAR FOR HOSPITAL AND NURSING BEDS

(75) Inventor: Svend Erik Knudsen Jensen, Sønderborg (DK)

(73) Assignee: Linak A/S (DK)

( * ) Notice: Subject to any disclaimer, the term of this patent is extended or adjusted under 35 U.S.C. 154(b) by 244 days.

(21) Appl. No.: 11/886,337

(22) PCT Filed: Nov. 15, 2006

(86) PCT No.: PCT/DK2006/000634
§ 371 (c)(1),
(2), (4) Date: Sep. 14, 2007

(87) PCT Pub. No.: WO2007/057014
PCT Pub. Date: May 24, 2007

(65) Prior Publication Data
US 2008/0195776 A1     Aug. 14, 2008

(30) Foreign Application Priority Data
Nov. 15, 2005    (DK) ................................ 2005 01583

(51) Int. Cl.
*G06F 13/42* (2006.01)
(52) U.S. Cl. .......................... 710/106; 700/3
(58) Field of Classification Search .................. 710/105, 710/110, 19; 700/3; 370/475, 476
See application file for complete search history.

(56) References Cited

U.S. PATENT DOCUMENTS

| 4,949,299 | A | | 8/1990 | Pickett |
| 5,311,508 | A | * | 5/1994 | Buda et al. ..................... 370/476 |
| 5,475,854 | A | * | 12/1995 | Thomsen et al. ............... 710/23 |
| 5,886,894 | A | | 3/1999 | Rakoff |
| 6,188,407 | B1 | * | 2/2001 | Smith et al. ................... 715/841 |

FOREIGN PATENT DOCUMENTS

| WO | 2006/032283 A1 | 3/2006 |
| WO | 2007/057420 | 5/2007 |

OTHER PUBLICATIONS

S. Linnman, "M35: The Local Network for Electric Wheelchairs and Rehabilitation Equipment" in IEEE Translations on Rehabilitation Engineering, vol. 4, No. 3, Sep. 1996, pp. 188-192.

* cited by examiner

*Primary Examiner* — Clifford Knoll
(74) *Attorney, Agent, or Firm* — Dykema Gossett PLLC

(57) ABSTRACT

The invention relates to a communications method of communicating states from an activation unit to a receiver via a communications bus, wherein the state may be activation/deactivation of an activation unit, and wherein the state is communicated to the receiver via a serial data stream timed by a clock signal, said data stream transmitting data packets which comprise an identification part and a data pare wherein: ● the identification part comprises a plurality of bits which identify which activation units the data packet concerns, and ● the data part comprises a plurality of bits which individually identify the state of an activation unit. The invention also relates to a system based on the communications method and comprising an activation unit and a receiver. In addition, the invention relates to an activation unit and a receiver.

14 Claims, 5 Drawing Sheets

COMMUNICATIONS METHOD, IN PARTICULAR FOR HOSPITAL AND NURSING BEDS

The invention relates to a communications method of communicating states from an activation unit to a receiver via a communications box, in particular for hospital beds and nursing beds as well as patient couches. The invention moreover relates to a system based on the communications method, comprising an activation unit and a receiver. In addition, the invention relates to an activation unit and a receiver.

BACKGROUND

For convenience, the disclosure of the invention will be based on a hospital bed, as known e.g. from EP 498 111 B2 to J. Nesbit Evans & Co. Ltd., in which the mattress supporting face may be adjusted to a contour by at least two actuators, and in which the frame, in which the mattress supporting face is mounted, may be raised and lowered as well as titled over a transverse axis (Trendelenburg positions) by two additional actuators. For the operation of the bed, there is a handset for the patient, or, as an alternative or as a supplement, a control panel may be incorporated in the guard rail. Likewise, a separate handset as well as a control box (called an ACP) may be provided for the staff, mounted at the foot end of the bed where the staff may read all adjustment functions. All these units are connected by individual multi-conductor cables to a central control box (CB), also called a control unit containing a control, a power supply intended for connection to the mains as well as a rechargeable battery pack so that the bed may function temporarily without being connected to the mains. Another example of a bed is shown in WO 01/47340 to Hill-Rom Services, Inc. An example of a simple therapy couch is disclosed in U.S. Pat. No. 5,014,688 to Tri W-G, Inc.

The control typically comprises a microprocessor and associated software adapted to the individual bed makes and the specific intended uses of the beds.

With many different units in an actuator system, the wiring is quite complicated and must be established with great care in order to avoid overloading in the movable mechanical parts. Further, connection of ever more units is also required, e.g. an additional actuator for the adjustment of the neck support, a device for the automatic turning of the patients, devices for counteracting bedsores, massage devices, sophisticated air mattresses, etc.

Thus, there is a wish for many keys (functions) on the handsets as well as many handsets parallel in the system.

A traditional system is characterized in that there is a direct connection from any handset function to the control unit. It is not so that the handset functions can only be arranged in one physical unit; these may very well be distributed on several handsets connected in parallel, but understood in the sense that for each function there is a key (activation unit), and it is connected directly.

A key may refer to a wire or to a switch between two wires (matrix handsets).

In the first case, a maximum of 8 functions (1 common as well as 8 signals) may thus be achieved with a normal 9-conductor cable. With the matrix type, a maximum of 20 keys (4×5 lines) may be achieved using 9 conductors. Typically, however, one of the conductors is used for grounding, and, therefore, only a 4×4 matrix corresponding to 16 keys can be used. Matrix handsets unfortunately have the drawback that several keys cannot be detected with certainty at the same time, as there is no unique decoding as to which keys are activated.

US 2003/0079289 A1 describes an adjustable bed particularly intended for severely overweight patients. The bed may be controlled by serial signals, where adjustments are written in a plurality of RAM circuits, and where the contents are read and executed periodically, controlled by an interrupt. This is a relatively complicated control, which requires a good deal of special features, and which is relatively complex to implement and extend with additional functionalities.

U.S. Pat. No. 6,396,224 B1 and U.S. Pat. No. 5,600,214 A describe other control systems for adjustable beds. Again, complex solutions are involved, where just one unit can be active at a time.

A further drawback of the foregoing is that they are all based on master-slave communication. This requires that all units in the system are known in advance, since these must have individual addresses in connection with the design of the communication.

OBJECT AND DISCLOSURE OF THE INVENTION

An object of the invention is to provide a solution to the above-mentioned problems.

This is achieved by a communications method of communicating states from an activation unit to a receiver via a communications bus, wherein the state may be activation/deactivation of an activation unit, and wherein the state is communicated to the receiver via a serial data stream timed by a clock signal. The data stream transmits data packets which comprise an identification part and a data part, wherein
  the identification part comprises a plurality of bits identifying which activation units the data packet concerns, and
  the data part comprises a plurality of bits which individually identify the state of an activation unit.

Hereby, parallel information is converted into a serial data stream. The clock signal may have a double function. A long pause in the clock signal indicates that a data packet is started. This packet is initiated by an identification consisting of e.g. 3 bits, which state the type. Then, 32 bits follow, where each bit corresponds to an activation unit which might e.g. be a key on a control unit for a hospital bed, and where the individual bit indicates whether the key is activated. In principle, the data stream may be made considerably longer or be shared by several data packets, whereby the state of an almost indefinite number of keys may be communicated, and where all may be read uniquely, irrespective of how many have been activated. The activation unit might also be a unit connected to the control unit which wishes to communicate its state to another unit.

The receiver may e.g. be the control unit, which uses the state indication from the activation unit for initiating a specific control, e.g. raising of the head of the bed, as long as the state of an activation unit is activated. The receiver might also be other units, e.g. the ACP, to which it is communicated by the method according to the invention that a specific safety setting is activated, and, therefore, a light-emitting diode in the ACP must be turned on to indicate this. Further, the receiver might be a Multi Junction Box (MJB), which reads the data signal and is activated—e.g. Under Bed Light on the basis of the state of an activation unit.

The system is characterized in that the individual bits are logic 0 when an activation unit is not activated. All activation units, however, have a facility of adding a logic 1, representing that the state of the activation unit is activated. In terms of structure, the communications bus may be designed so that all can contribute with a logic 1 at every bit position.

Thus, it is characteristic of the bus that the data stream is not provided with e.g. a check sum or other safety forms, since all units can contribute with active keys. Hereby, a relatively modest processor overhead suffices.

The very simple communications protocol here makes it possible to make a hardware realization of a handset unit at very low cost.

In an embodiment, the identification part of the data packet is changed from data packet to data packet. Hereby, the purpose of the data packet may be changed.

In an embodiment, the identification part of the data packets is changed in a periodical sequence. This ensures a continuous optimization, and with a period time of e.g. 30 ms all data are transported currently.

The invention moreover relates to a storage medium comprising instructions which enable a computer to execute the method as described above.

Further, the invention relates to a system comprising an activation unit and a receiver, wherein the activation unit is capable of communicating states to the receiver via a communications bus, and wherein the state may be activation/deactivation of the activation unit, said system additionally comprising:
    a master unit comprising
        means for generating a clock signal for timing a serial data stream on the communications bus,
        means for generating a serial data stream comprising data packets with an identification part and a data part, said identification part comprising a plurality of bits which identify activation units which the data packet concerns, said data part comprising a plurality of bits which individually identify the state of the activation units,
    the activation unit is additionally associated with
        means for reading the identification part,
        means for changing a bit in the data part, if the identification part identifies the activation unit, and if the state of the activation part is activated,
    the receiver is additionally associated with
        means for reading the identification part,
        means for reading a bit in the data part, if the identification part identifies an activation unit associated with the receiver.

In addition, the invention relates to an actuator system comprising a system according to the invention. Particularly in connection with actuator systems in connection with e.g. hospital and nursing beds as well as therapy couches, the invention may be used to advantage, since, typically, there are some operating options.

Moreover, the invention relates to an activation unit for communicating states from the activation unit to a receiver, wherein the state may be activation/deactivation of the activation unit, and wherein the states are communicated to the receiver via a serial data stream timed by a clock signal, said data stream transmitting data packets which comprise an identification part and a data part, said identification part comprising a plurality of bits which identify activation units which the data packet concerns, said data part comprising a plurality of bits which individually identify the state of the activation units, said activation unit additionally comprising:
    means for reading the identification part,
    means for changing a bit in the data part, if the identification part identifies the activation unit, and if the state of the activation part is activated.

An activation unit might e.g. be an operating unit with a key, alternatively, an operating unit might comprise a plurality of activation units (keys).

Further, the invention relates to a receiver for use in a system comprising an activation unit, wherein the activation unit is capable of communicating states to the receiver via a communications bus, wherein the state may be activation/deactivation of the activation unit for communicating states from the activation unit to the receiver, wherein the state may be activation/deactivation of the activation unit, and wherein the states are communicated to the receiver via a serial data stream timed by a clock signal, said data stream transmitting data packets which comprise an identification part and a data part, said identification part comprising a plurality of bits which identify activation units which the data packet concerns, said data part comprising a plurality of bits which individually identify the state of the activation units, said receiver additionally comprising:
    means for reading the identification part,
    means for reading a bit in the data part, if the identification unit identifies an activation unit associated with the receiver.

The receiver might e.g. be the control unit connected to the operating units in connection with e.g. a hospital bed. The receiver might additionally comprise a master unit as described above.

BRIEF DESCRIPTION OF DRAWINGS

The invention will be described below with reference to the figures, in which.

DESCRIPTION OF EMBODIMENTS

Figure 1:
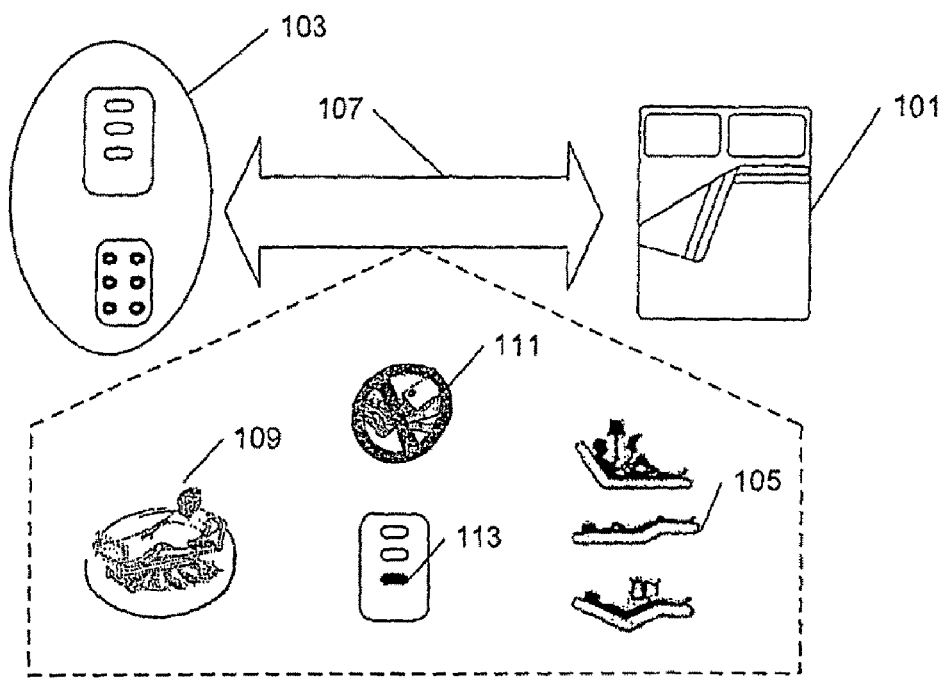
FIG. 1 illustrates a hospital bed and the operation of it.

FIG. 1 illustrates a hospital bed 101, and this may be operated via one or more operating units 103. One type of operating unit is the handset (HB), which allows the patient in the hospital bed to adjust the various parts of the bed, including the height, the angle of the backrest section and the angle of the legrest section 105. In connection with hospital beds there may also be a special operating unit (ACP (Attendant Control Panel), which is only accessible to the hospital staff, and which, in addition to the adjustment of the bed, also provides the option of locking specific adjustment possibilities depending on the patient. The blocking functionality is special, the object being to prevent the patient from adjusting the bed improperly 111. There may also be other operating units; in connection with e.g. a dentist's chair or a hairdresser's chair there may be a foot control. Typically, the operating units comprise a plurality of keys (activation units), and the function of these depend specifically on how these are coupled to the bed.

In addition to the use of operating units for operating the ergonomic adjustment 107 of the bed, there may also be other units, which might optionally be controlled from the controls—including:

- turning on/off of light in the form of either a reading lamp or an orientation lamp below the bed 109 (Under Bed Light)
- adjustment of the intensity of light via e.g. two keys—one for brightening and one for dimming the light.
- nurse call, where the patient has the possibility of calling staff when this is needed.

In addition to communication from the operating units to the bed, there may also be communication from the bed to the operating units—the keys may inter alia have a blocking light 113 indicating that the adjustment of the unit they represent, is blocked.

Figure 2:
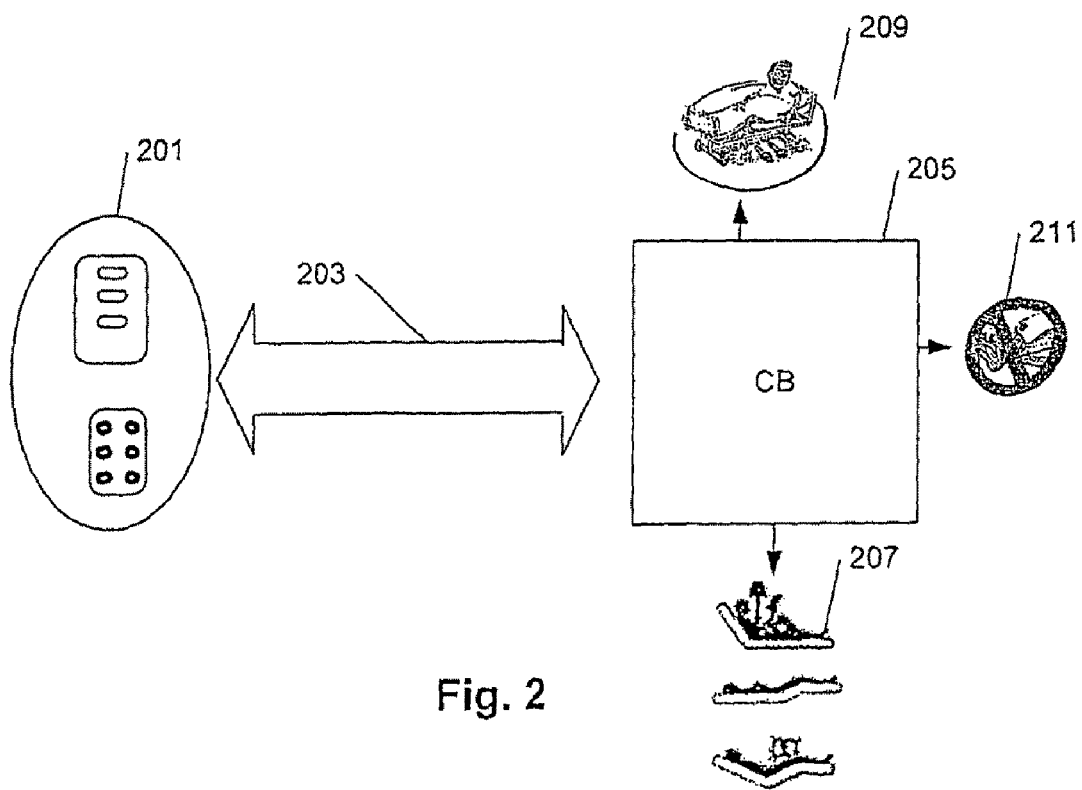
FIG. 2 shows the communication between operating units and a control unit.

In connection with hospital beds, the operating units 201 communicate 203 with a control unit (CB) 205, and this is shown in FIG. 2. The control unit (CB) 205 e.g. receives input from the operating units 201, and ensures subsequently that the associated action is performed. This might e.g. be an activation of the raising of a bed head 207. When a key on an operating unit 201 representing this functionality is activated, a signal is applied to the control unit 205, and the control unit then ensures that precisely the actuator or actuators which adjusts/adjust the backrest section is/are activated. If it is not an adjustment of the setting of the bed, but instead an activation of light under the bed 209, it works in that a key (activation unit) on an operating unit 201 representing activation of this functionality is activated, and a signal is applied to the control unit 205, following which the control unit transmits a signal to the light part for activating this. A further example might be blocking of an adjustment for safety reasons 211. When a key on an operating unit 201 representing this functionality is activated, a signal is applied to the control unit 205, and the control unit is then effective to block precisely the actuator or actuators which regulates/regulate precisely this adjustment. In this connection, a signal might additionally be sent back to the operating unit for activating a light in the activated key.

The invention also relates to a communications protocol which may be used in connection with the above-mentioned communication between the activation units and the receivers. The protocol will be described below in connection with a control system for hospital beds, but the protocol may also be used generally in connection with systems for the adjustment of furniture, such as e.g. dentist's chairs, beds, armchairs, etc.

Figure 3:
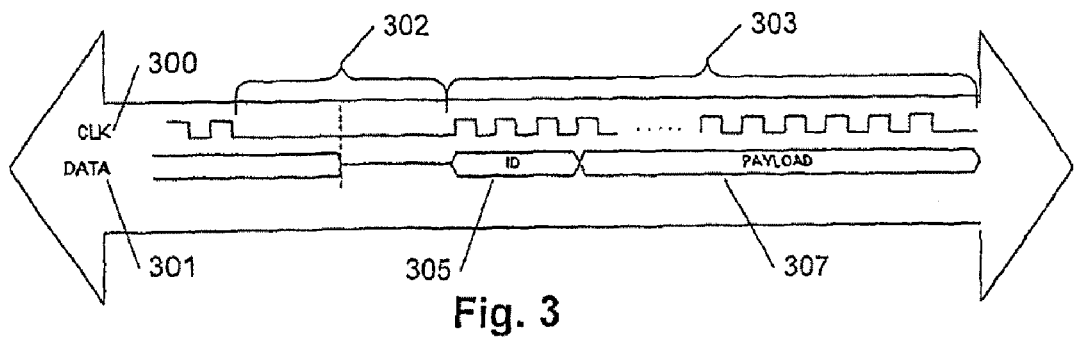
FIG. 3 shows a data signal and a clock signal in a communications protocol according to the invention.

FIG. 3 illustrates a data signal as it looks in connection with a protocol according to the invention. The protocol requires the presence of a master unit which transmits a synchronous clock signal 300 and a data signal 301. The clock signal has two functions; it is to indicate that a new data packet 303 is started—and in an embodiment this is done by making a pause 302 of e.g. 5 clock periods—and the clock signal 300 also provides for timing the subsequent data packet 303. The data packet 303 is composed of a first identification part 305 identifying which units (handset, ACP, etc.) the subsequent data part concerns, and a subsequent data part 305 which represents the states of the units (which activation units on the handset are activated, which keys are to flash, etc.)

Figure 4:
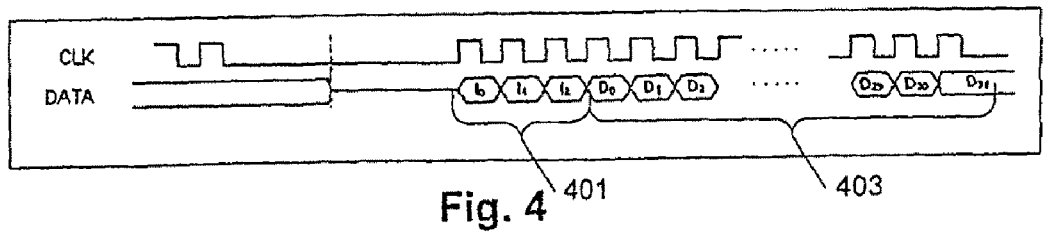
FIG. 4 shows the structure of a data packet in a communications protocol according to the invention.

FIG. 4 illustrates an embodiment of the structure of the data packet. The data packet consists of 3 identification bits ($I_0$, $I_1$, $I_2$) 401 and subsequently of 32 data bits ($D_0$, $D_1$ ..., $D_{31}$) 403.

It is the master unit which determines which data packets are to be transmitted with the data signal, and thus it is the master unit which provides for the filling of identification bits. Identification bits identify the type of data in the subsequent data bits. It is shown in the table below how three identification bits might be used:

| Name | $I_o$ | $I_1$ | $I_2$ |
|---|---|---|---|
| HB | 0 | 0 | 0 |
| ACP | 1 | 0 | 0 |
| DATA | 0 | 1 | 0 |
| Service | 1 | 1 | 0 |
| Reserved 1 | 0 | 0 | 1 |
| Reserved 2 | 1 | 0 | 1 |
| Reserved 3 | 0 | 1 | 1 |
| Reserved 4 | 1 | 1 | 1 |

There are 4 types of data packets which are HB, ACP, DATA and SERVICE, respectively. In addition, an additional 4 is reserved for future use.

An example is shown below where identification bits identify that the subsequent data bits concern a handset. The master unit fills the identification part, and the value of the subsequent bits depends on which keys are activated on the handset. Each of the 32 bits represents a function or a key on a handset, and if the key is activated, the bit value is set high (1). When a key is not activated, the bit value automatically goes to low (0). An embodiment of this is explained in connection with FIG. 7.

| | ID | | | Data from handset (HB) | | | | | | |
|---|---|---|---|---|---|---|---|---|---|---|
| Bit | $I_0$ | $I_1$ | $I_2$ | $H_0$ | $H_1$ | $H_2$ | $H_3$ | $H_4$ | $H_5$ ... | $H_{31}$ |
| Value | 0 | 0 | 0 | 1 | 0 | 0 | 1 | 0 | 0 ... | 0 |

In the example below, key 1 and key 4 are activated, and the remaining keys are not activated. All bits in the data part might represent keys on a handset, but it might also represent a number of handsets with keys. The individual bits just represent an activated key, and then it is the receiver which translates this into a function.

An example is shown below where identification bits identify that the subsequent data bits concern an ACP:

| | ID | | | Data to ACP | | | Data from ACP | | |
|---|---|---|---|---|---|---|---|---|---|
| Bit | $I_0$ | $I_1$ | $I_2$ | $A_0$ | $A_1$ ... | $A_{15}$ | $A_{16}$ | $A_{17}$ ... | $A_{31}$ |
| Value | 1 | 0 | 0 | | | | | | |

In addition to data from the ACP which identify which keys are activated corresponding to the handsets, there are also data to the ACP. This might e.g. be an indication that a key on the ACP is to flash, since a blocking is activated.

An example is shown below where identification bits identify that the subsequent data bits concern data:

| | ID | | | Data | | | | | | |
|---|---|---|---|---|---|---|---|---|---|---|
| Bit | $I_0$ | $I_1$ | $I_2$ | $D_0$ | $D_1$ | ... | $D_{15}$ | $D_{16}$ | $D_{17}$ | ... $D_{31}$ |
| Value | 0 | 1 | 0 | | | | | | | |

This type of data packet is an open part and is used for communication between units. The 32 bits may be used for all forms of data between e.g. a control unit and other units.

An example is shown below where identification bits identify that the subsequent data bits concern service data:

| | ID | | | Type | | | R/W | Data | | |
|---|---|---|---|---|---|---|---|---|---|---|
| Bit | $I_0$ | $I_1$ | $I_2$ | $S_0$ | $S_1$ | $S_2$ | $S_3$ | $S_4$ | $S_5$ | ... $S_{31}$ |
| Value | 1 | 1 | 0 | | | | | | | |

Service data are used for service, and the first 3 data bits ($S_0$, $S_1$, $S_2$) identify which unit the service data concern. Data bit $S_3$ identifies whether reading or writing to the unit is to be performed, and, finally, bits $S_4$-$S_{31}$ indicate which information is to be read or written.

Thus, there is a number of various types of data packets which are identified by identification bits, and the master unit must thus currently provide for switching between the individual data packet types by changing the value of the identification bits.

Figure 5:
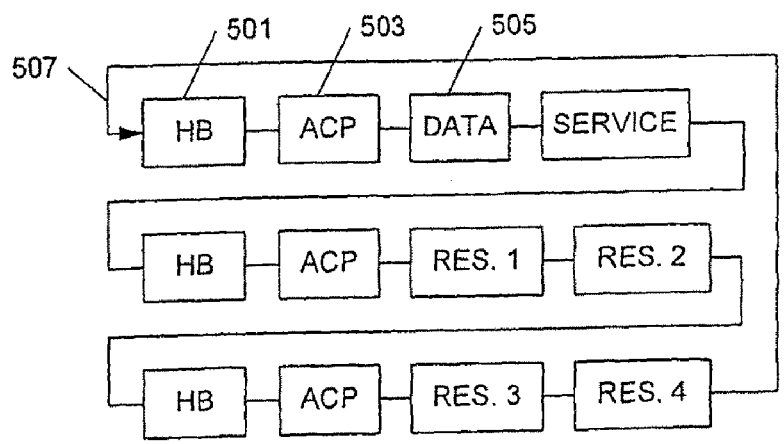
FIG. 5 shows the order in which the various data packets may be transmitted from the master unit.

FIG. 5 illustrates an example of this. Here, identification bits are initially 501 set to indicate that data from a handset (HB) are involved. Then 503, it is data to/from an ACP. Then 505 it is an open data packet, and the process proceeds in this manner through the various data types. When all data types have been handled in a predetermined order (sequence), the process recommences 507, and thereby identification bits are changed in a periodic sequence. The order depends on the individual system and is set up in the master unit.

Figure 6:
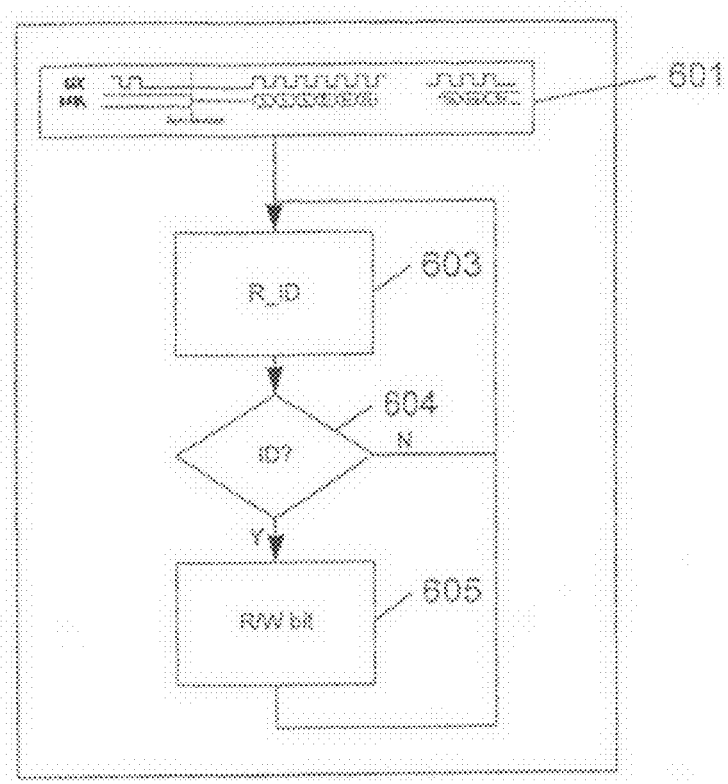
FIG. 6 shows how units write and read, respectively, data in a data packet in a communications protocol according to the invention.

FIG. 6 shows an example of how a unit, e.g. in the form of an activation unit or a receiver, uses the data signal. In 603, the unit reads identification bits in the data signal, inter alia by means of the clock signal. In 604, it is checked whether identification bits concern the unit, and if this is not the case (N), no further steps are taken, and just the process of reading identification bits in the data signal continues. If it turns out in 604 that identification bits concern the unit (Y), then predefined bits are read into the data part, or the value of a bit is set to 1. If e.g. the unit is a handset, and a key (activation unit) is activated on the handset, the data packet concerning data from the handset is awaited. This is identified by identification bits in the data packet. Then, the bit in the data part corresponding to the activated key is set to 1. Correspondingly, the control unit might subsequently read the contents of the data packet and initiate a function corresponding to the bit which has been set to 1.

Figure 7:
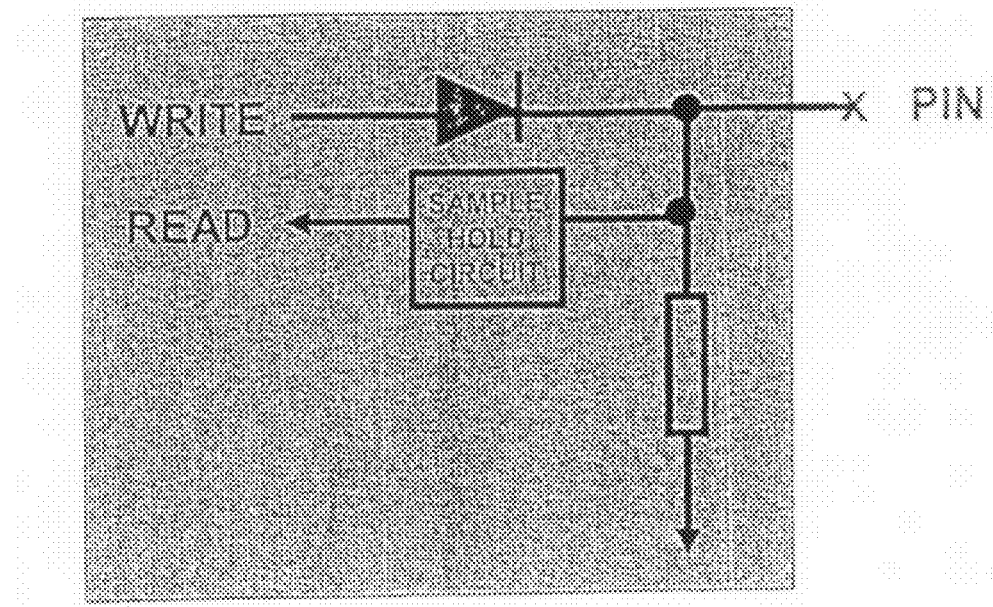
FIG. 7 shows the logic structure of a pin, when the units communicating with a communications protocol are connected via a 32 pin connector.

The units in a system using the protocol according to the invention, may be interconnected via a 32 pin connector, and the logic structure of a pin of such a connector is shown in FIG. 7. Each pin may add a high signal, but it is not possible to force an 0 because of the logic structure.

Figure 8:
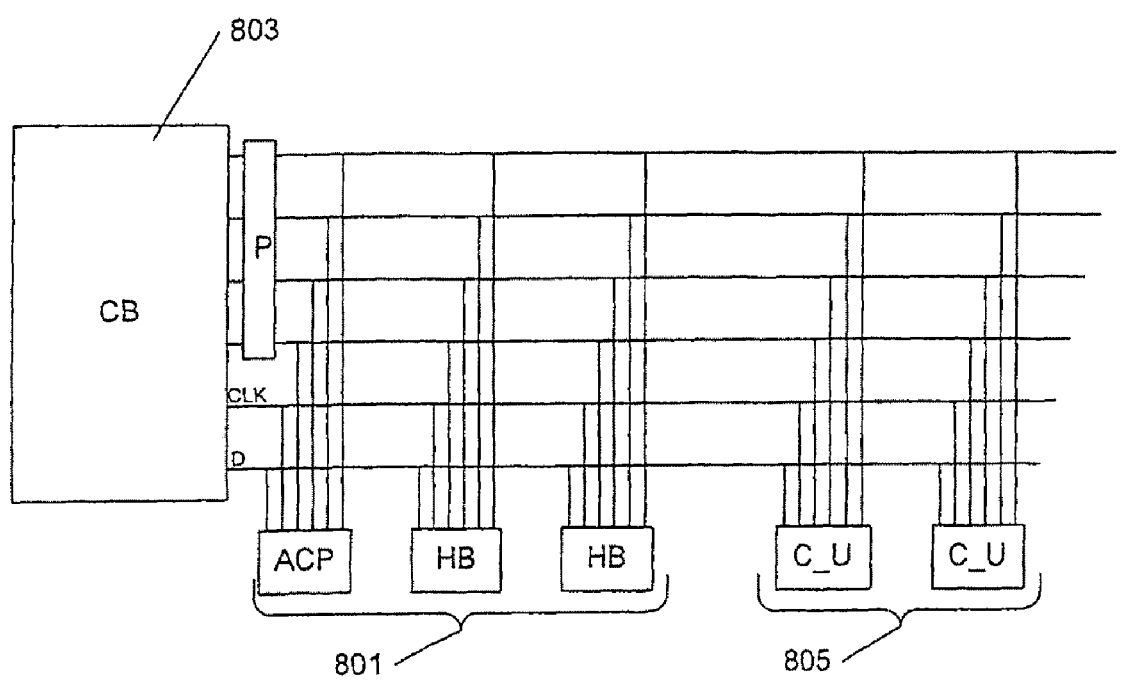
FIG. 8 shows how the operating units are connected to a control unit, when these communicate with a communications protocol according to the invention.

It is shown in FIG. 8 how the operating units 801 are connected to a control unit 803. In addition to a power supply, there are two active wires, clock (CLK) and data (D). A unique option is that the protocol is open to customerized equipment 805, allowing communication directly on the bus with an arbitrary unit.

Figure 9:
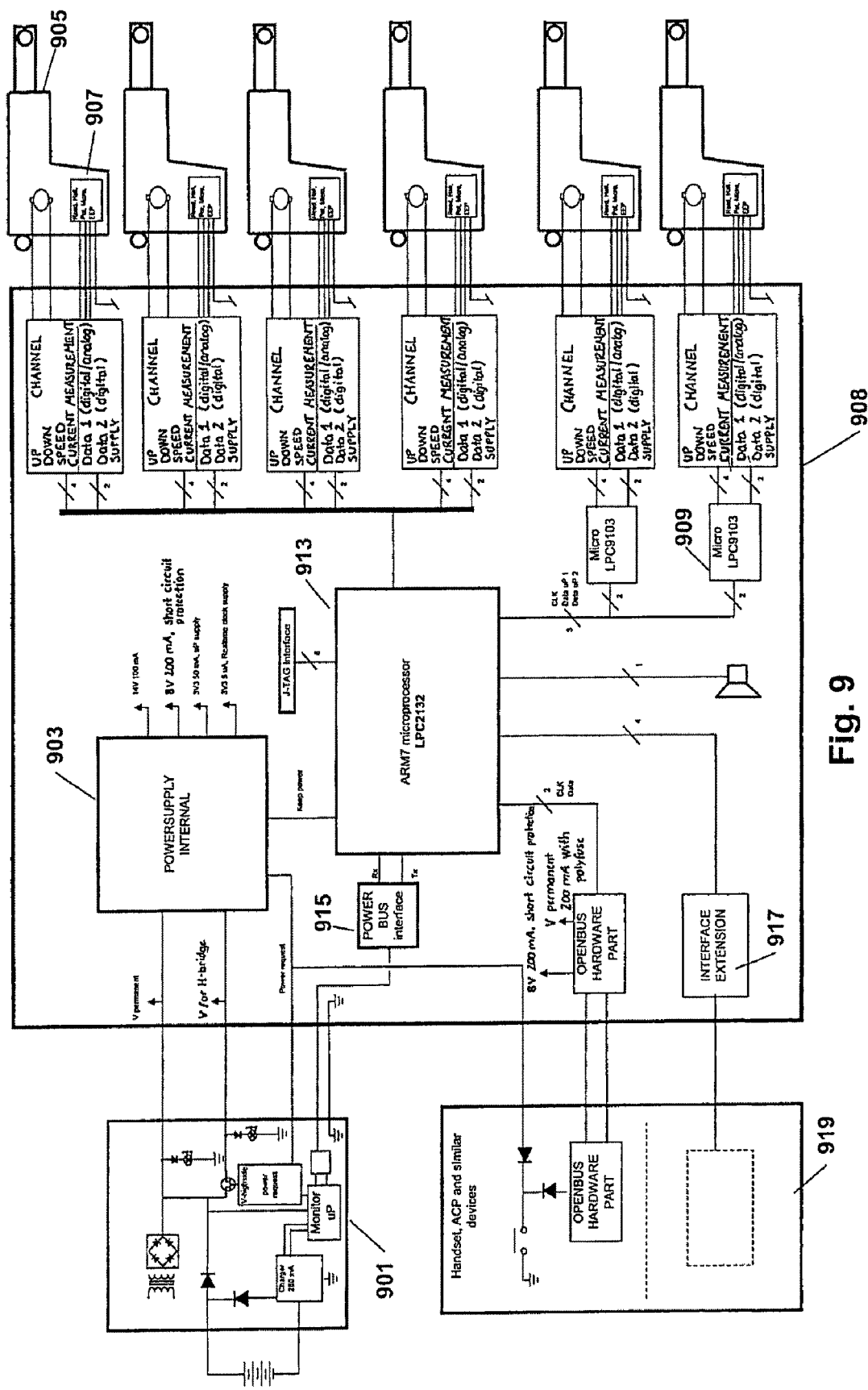
FIG. 9 shows an embodiment of an actuator system for a hospital bed, where a communications protocol according to the invention is used.

FIG. 9 shows an actuator system for a hospital bed, and the system comprises an external power supply 901 for connection to the mains and a rechargeable battery pack, just as it comprises an internal power supply 903. The system moreover comprises a plurality of actuators for adjusting the bed, said actuators 905 having a processor 907. The control unit 908 of the system comprises a processor 909 for two of the actuators. In addition, the system comprises a buzzer 911. There are interface extensions 917 for peripheral equipment 919 from the overall processor 913 of the control unit 908, connected to the external power supply by a power bus 915. The peripheral equipment communicates with the control unit as described above.

A communications protocol is described above for use in a system comprising a control unit, a plurality of operating units and a master unit. In an embodiment, the master unit might be a dedicated separate unit, but it might also be an integrated part of either the control unit or the operating units. Of course, the communication may be extended to communication between additional units, including multi-junction box (MJB), which reads the data signal and activates e.g. Under Bed Light on the basis of the state of an operating unit.

The invention claimed is:

1. A method for adjusting adjustable articles of furniture wherein said adjusting is performed by communicating between operating units and a receiver, wherein:
   the adjusting is performed by communicating states from activation units on said operating unit to said receiver via a communications bus, wherein the state may be activation/deactivation of an activation unit, the state is communicated to the receiver via a serial data stream timed by a clock signal, and the data stream transmits data packets comprising an identification part and a data part, wherein:
   the identification part comprises a plurality of bits which identify which type of operating unit the data packet concerns, and
   the data part comprises a plurality of bits which individually identify the state of an activation unit on said operating unit.

2. The method according to claim 1, wherein the data part identifies an activated activation unit with a logic 1 and a deactivated activation unit with a logic 0.

3. The method according to claim 1, wherein bits in the data part are set to logic 1 if the activation unit is activated, otherwise said bits are logic 0.

4. The method according to claim 1, wherein the activation unit is a switch in the form of a key on an operating unit which may be activated or deactivated.

5. The method according to claim 1, wherein the identification part of the data packet is changed from data packet to data packet.

6. The method according to claim 5, wherein the identification part of the data packets is changed in a periodic sequence.

7. A storage medium comprising instructions which enable a computer to execute the method according to claim 1.

8. An actuator system comprising an operating unit and a receiver for adjusting adjustable articles of furniture, wherein activation units on said operating unit are activated/deactivated when adjusting said furniture and are capable of communicating states to the receiver via a communications bus, and wherein the state may be activation/deactivation of the activation unit, said system additionally comprising:
a master unit comprising
means for generating a clock signal for timing a serial data stream on the communications bus used for communicating said states,
means for generating a serial data stream comprising data packets with an identification part and a data part, said identification part comprising a plurality of bits which identify which type of operating units the data packet concerns, said data part comprising a plurality of bits which individually identify the state of the activation units on said operating unit,
the operating unit is additionally associated with
means for reading the identification part,
means for changing a bit in the data part, if the identification part identifies an activation unit on said operating unit, and if the state of the activation unit is activated, and
the receiver is additionally associated with
means for reading the identification part,
means for reading a bit in the data part, if the identification part identifies an operating unit associated with the receiver,
means for initiating adjustment of said furniture based on said bit in said data part.

9. The actuator system comprising a system according to claim 8.

10. A hospital and nursing bed comprising an actuator system according to claim 8.

11. The receiver according to claim 8, wherein said receiver additionally comprises a master unit comprising:
means for generating a clock signal for timing the serial data stream on the communications bus,
means for generating a serial data stream comprising data packets with an identification part and a data part, said identification part comprising a plurality of bits which identify activation units which the data packet concerns, said data part comprising a plurality of bits which individually identify the state of the activation units.

12. An operating unit for adjusting adjustable articles of furniture where an operating unit is configured to communicate states from activation units on said operating unit to a receiver, wherein activation units on said operating unit are activated/deactivated when adjusting said furniture and wherein the state may be activation/deactivation of the activation unit, and wherein the states are communicated to the receiver via a serial data stream timed by a clock signal, said data stream transmitting data packets which comprise an identification part and a data part, said identification part comprising a plurality of bits which identify the type of operating unit the data packet concerns, said data part comprising a plurality of bits which individually identify the state of an activation unit on said operating unit, said operating unit being additionally associated with:
means for reading the identification part, and
means for changing a bit in the data part, if the identification part identifies the operating unit, and if the state of an activation unit on said operating unit is activated.

13. A receiver for use in a system comprising an operating unit for adjusting adjustable articles of furniture, wherein activation units on said operating unit are activated/deactivated when adjusting said furniture and wherein the operating unit is capable of communicating states from activation units on said operating unit to the receiver via a communications bus, wherein the state may be activation/deactivation of the activation unit, and wherein the states are communicated to the receiver via a serial data stream timed by a clock signal, said data stream transmitting data packets which comprise an identification part and a data part, said identification part comprising a plurality of bits which identify which type of operating units the data packet concerns, said data part comprising a plurality of bits which individually identify the state of an activation unit on said operating unit, said receiver being additionally associated with:
means for reading the identification part,
means for reading a bit in the data part, if the identification part identifies an operating unit associated with the receiver, and
means for initiating adjustment of furniture based on said bit in said data part.

14. An adjustable article of furniture, said furniture comprising an actuator system comprising an operating unit and a receiver for adjusting said adjustable article of furniture, wherein activation units on said operating unit are capable of communicating states to the receiver via a communications bus, and wherein the state may be activation/deactivation of the activation unit, said system additionally comprising:
a master unit comprising
means for generating a clock signal for timing a serial data stream on the communications bus,
means for generating a serial data stream comprising data packets with an identification part and a data part, said identification part comprising a plurality of bits which identify which type of operating units the data packet concerns, said data part comprising a plurality of bits which individually identify the state of the activation units on said operating unit,
the operating unit is additionally associated with
means for reading the identification part,
means for changing a bit in the data part, if the identification part identifies an activation unit on said operating unit, and if the state of the activation unit is activated, and
the receiver is additionally associated with
means for reading the identification part,
means for reading a bit in the data part, if the identification part identifies an operating unit associated with the receiver.

* * * * *